United States Patent
Namba et al.

(10) Patent No.: US 6,541,029 B1
(45) Date of Patent: Apr. 1, 2003

(54) NUTRIENT INFUSION PREPARATION

(75) Inventors: Ryohei Namba, Osaka (JP); Shunzo Yamashita, Osaka (JP); Takeo Kikuchi, Osaka (JP); Makoto Sato, Osaka (JP)

(73) Assignee: Nipro Corporation, Osaka (JP)

( * ) Notice: Subject to any disclaimer, the term of this patent is extended or adjusted under 35 U.S.C. 154(b) by 0 days.

(21) Appl. No.: 09/386,518

(22) Filed: Aug. 31, 1999

(30) Foreign Application Priority Data

Aug. 31, 1998 (JP) .................................... 10-246108

(51) Int. Cl.⁷ .......................... A61K 9/00; A61K 9/127; A61K 9/14; A61K 9/66

(52) U.S. Cl. .................. 424/450; 424/400; 424/455; 424/489

(58) Field of Search ................. 424/400, 450, 424/455, 489

(56) References Cited

U.S. PATENT DOCUMENTS

| | | | | |
|---|---|---|---|---|
| 4,280,996 A | | 7/1981 | Okamato et al. | 424/199 |
| 5,098,606 A | * | 3/1992 | Nakajima et al. | 252/358 |
| 5,662,932 A | * | 9/1997 | Amselem et al. | 424/450 |
| 5,674,527 A | * | 10/1997 | Inoue et al. | 424/450 |
| 5,753,241 A | * | 5/1998 | Ribier et al. | 424/401 |

FOREIGN PATENT DOCUMENTS

| | | | |
|---|---|---|---|
| EP | 0 711 556 A1 | * | 5/1996 |
| WO | 2 455 888 A1 | | 12/1980 |
| WO | 2 497 668 A1 | | 7/1982 |
| WO | 0 144 434 A1 | | 6/1985 |
| WO | 0 211 258 A2 | | 2/1987 |
| WO | 0 625 313 A1 | | 11/1994 |

OTHER PUBLICATIONS

Abstract, JP2167217, Publication Date: Jun. 27, 1990.
Patent Abstracts of Japan, Pub. No. 05009111, Pub. Date: Jan. 19, 1993.
Patent Abstracts of Japan, Pub. No. 05032540, Pub. Date: Feb. 9, 1993.
Patent Abstracts of Japan, Pub. No. 06092861, Pub. Date: Apr. 5, 1994.
Patent Abstracts of Japan, Pub. No. 06279290, Pub. Date: Oct. 4, 1994.
Patent Abstracts of Japan, Pub. No. 06312923, Pub. Date: Nov. 8, 1994.

(List continued on next page.)

*Primary Examiner*—Thurman K. Page
*Assistant Examiner*—S. Tran
(74) *Attorney, Agent, or Firm*—Kubovcik & Kubovcik

(57) ABSTRACT

A nutrient infusion preparation comprises a fat emulsion essentially consisting of fat particles having a mean particle size of 0.003 to 0.100 μm and a dispersion medium, and a solution containing electrolytes and amino acids. Also the nutrient infusion preparation comprises a fat emulsion (A) consisting essentially of fat particles having a mean particle size of 0.003 to 0.100 μm and a dispersion medium, and a solution (B) containing electrolytes and/or amino acids. A container having a plurality of chambers which are isolated from each other by partitions capable of being easily opened, whose respective chambers contain the fat emulsion (A) and said solution (B) and optionally a solution (C) containing saccharides. The infusion preparation of the present invention supplies various nutrient components including fatty acids required biologically to patients and enables amelioration or prevention of essential fatty acid deficiencies during TPN therapy. Further, the infusion preparation enables visual identification of insoluble foreign bodies present in an infusion container and can be administered to patients through a sterilization filter.

12 Claims, 2 Drawing Sheets

OTHER PUBLICATIONS

Patent Abstracts of Japan, Pub. No. 07178151, Pub. Date: Jul. 18, 1995.

Patent Abstracts of Japan, Pub. No. 07277989, Pub. Date: Oct. 24, 1995.

Francoise Soges Bettner, M.S. et al., "Effects of pH Temperature, Concentration, and Time . . . ", *J. Parenteral and Enteral Nutrition*, vol. 10, No. 4, pp. 375–380, 1986.

Kathleen R. Harrie et al., "Comparison of Total Nutrient Admixture . . . ", *J. Parenteral and Enteral Nutrition*, vol. 10, No. 4, pp. 381–387, 1986.

Patent Abstracts of Japan; Publication No. 08–182739; Publication Date: Jul. 16, 1996.

Patent Abstracts of Japan; Publication No. 08–191873; Publication Date: Jul. 30, 1996.

\* cited by examiner

NUTRIENT INFUSION PREPARATION

FIELD OF THE INVENTION

The present invention relates to an integrated nutrient infusion preparation for total parenteral nutrition (TPN) therapy. By the infusion preparation according to the present invention, an essential fatty acid deficiency can be ameliorated or prevented while supplementing various nutritional components that are biologically required. In addition, an appreciable transparency of the nutrient infusion preparation enables a visual identification of insoluble foreign bodies present in an infusion container as well as administration through a sterilization filter to a patient, whereby a marked advantage is exerted.

BACKGROUND OF THE INVENTION

A method for supplementing nutrition to a patient who is hospitalized due to a disease or injury has been conventionally an oral administration, which is the most natural and desirable method. However, to a patient for whom it is completely impossible to take nutrition orally for a prolonged period, a TNP solution containing various nutritional components such as saccharides, electrolytes and amino acids is administered generally via the central vein of the patient.

A TPN solution is administered to a patient usually after mixing saccharides, electrolytes and amino acids with each other to obtain the infusion preparation aseptically in a pharmaceutical laboratory in a hospital. Since this mixing procedure for obtaining the infusion preparation is complicated, the infusion preparation is contained in a multi-chamber container in which saccharides, electrolytes and amino acids have previously been filled but the saccharides and the amino acids have been separately filled because of their interaction. The multi-chamber container such as plastic containers having a plurality of chambers have already been developed and marketed for the purpose of saving the effort in the complicated procedure described above as well as preventing an invasion of microorganisms during the mixing procedure.

However, a patient who is administered with only a TPN solution containing various nutritional components such as saccharides, electrolytes and amino acids for a prolonged period will exhibit the symptoms of an essential fatty acid deficiency such as scale efflorescence, eczematoid eruption, retarded wound healing, thrombocytopenia, fat swelling, anemia, susceptibility to infection, increased water intake without increasing urine volume, growth disturbance, impotenia generandi and the like, which are problematic during TPN therapy. In addition, an essential fatty acid deficiency which is rare in a human living a routine life is observed frequently in a patient receiving only transvenous nutrition, and is developed within a period of 4 to 6 weeks especially when an energy source is only saccharides. Such essential fatty acid deficiency can be avoided by administering an essential fatty acid-rich fat emulsion concomitantly during TPN therapy.

It has been believed that the essential fatty acid deficiency can be prevented or ameliorated by daily administration of 50 to 100 mL of a 10% fat emulsion. In clinical practice, 200 to 500 mL of a 10% or 20% fat emulsion are given 2 or 3 times a week (Mascioli et al., Eur. J.Clin. Nutr, 51, 232–242 (1997), Tsukamoto et al., JJPEN, 14, (2) 135–138 (1992), Saito et al., JJPEN, 14 (2), 143(1992), Hiramatsu et al., NIPPON RINSHO, 49 (special edition), 125–129 (1991) , Yoshimoto et al., Medical Practice, 7, 114–122 (1990), A.Tashiro, PEN, 15 (2), 19–21 (1997)).

In a method for administering a fat emulsion during TPN therapy, a TPN solution is mixed directly with a fat emulsion, or a fat emulsion is introduced via a TPN infusion line, or it is injected separately via the peripheral vein.

While the essential fatty acid deficiency can be prevented by combining a TPN solution with a fat emulsion as discussed above, mixing of the fat emulsion with the electrolytes infusion causes an aggregation of particles due to the presence of divalent cations such as calcium ions or magnesium ions in the electrolytes. And mixing of the fat emulsion with amino acids also causes an aggregation of the fat particles due to the presence of basic amino acids such as arginine, lysine or histidine similarly to the above electrolytes. The resultant aggregation of fat, when administered to a living body may cause adverse reactions such as an embolism of a pulmonary capillary vessel. Accordingly, mixing of a TPN solution with a fat emulsion should be carried out carefully, for example, by ensuring consumption within 24 hours.

A commercially available fat emulsion is opaque like milk. As a result, a high TPN solution that is incorporated with the fat emulsion appears opaque even if the amount of the fat emulsion is small. Thus, it is impossible to identify insoluble foreign bodies, if any, in the TPN solution. Accordingly, the United State Food and Drug Administration FDA) recommended on Apr. 18, 1994 that a fat emulsion should be given by a different route entirely from that for an infusion preparation containing saccharides, electrolytes and amino acids.

A TPN solution is administered to a patient generally after filtration through a sterilization filter having a pore size of 0.2 to 0.45 $\mu$m in order to prevent contamination with microorganisms. However, it is difficult to filter the fat emulsion to be incorporated in the TPN solution through a sterilization filter having a pore size of 0.2 to 0.45 $\mu$m, since it contains fat particles having a mean particle size usually of about 0.200 to 0.300 $\mu$m together with rough particles having a size as large as 1.000 $\mu$m or greater. Accordingly, there is no option practically but to use a filter having a pore size of 1.2 $\mu$m which can filter the fat emulsion before administration in order to remove aggregated fat particles, foreign bodies and large-sized microorganisms such as Candida albicans species.

Because of the above described reasons, it has been difficult to provide a TPN solution containing fat as a single-component product, in spite of the fact that administration of the fat emulsion is effective in preventing an essential fatty acid deficiency during TPN therapy.

SUMMARY OF THE INVENTION

In the course of formulating a TPN solution containing a fat emulsion, we discovered, based on the fact that it is necessary to store the fat emulsion, electrolytes and amino acids separately until the time just before use, that the problems discussed above can be solved by storing the fat emulsion, the electrolytes and the amino acids separately in a plurality of chambers in a flexible plastic container and by using a fat emulsion consisting essentially of particles whose mean particle size is smaller than that of a conventional fat emulsion, thus establishing the present invention.

Thus, one embodiment of the present invention is a nutrient infusion preparation comprising a fat emulsion consisting essentially of fat particles having a mean particle size of 0.003 to 0.100 $\mu$m and a dispersion medium, and a solution containing electrolytes and/or amino acids. The former emulsion is separated from the latter solution and the emulsion and solution are mixed with each other just before administration to a patient.

Also, another embodiment of the present invention is a nutrient infusion preparation comprising a fat emulsion (A) consisting essentially of fat particles having a mean particle size of 0.003 to 0.100 μm and a dispersion medium, and a solution (B) containing electrolytes and amino acids.

Furthermore, another embodiment of the present invention is a nutrient infusion preparation comprising a fat emulsion (A) consisting essentially of fat particles having a mean particle size of 0.003 to 0.100 μm and a dispersion medium, a solution (B-1) containing electrolytes and a solution (B-2) containing amino acids.

Another embodiment of the present invention is a container for a nutrient infusion preparation which is characterized by having a plurality of chambers isolated from each other by partitions capable of being easily opened, wherein one chamber contains a fat emulsion consisting essentially of fat particles having a mean particle size of 0.003 to 0.100 μm and a dispersion medium, and the other chamber contains a solution containing electrolytes and/or amino acids.

Furthermore, another embodiment of the present invention is a container for a nutrient infusion preparation having a plurality of chambers which are isolated from each other by partitions capable of being easily opened, wherein one chamber contains a fat emulsion (A) consisting essentially of fat particles having a mean particle size of 0.003 to 0.100 μm and a dispersion medium, and the other chamber contains a solution (B) containing electrolytes and amino acids.

Furthermore, a further embodiment of the present invention is a container for a nutrient infusion preparation which is characterized by having a plurality of chambers isolated from each other by partitions capable of being easily opened, wherein one chamber contains a fat emulsion (A) consisting essentially of fat particles having a mean particle size of 0.003 to 0.100 μm and a dispersion medium, and the other chambers respectively contain a solution (B-1) containing electrolytes and a solution (B-2) containing amino acids.

The present invention also provides a method for producing a solution containing a fat emulsion comprising coarsely emulsifying a fat using a high speed agitating homogenizer in the presence of saccharides and/or polyhydric alcohols, adding a water for injection and finely emulsifying the resultant coarse emulsion using a high pressure spray homogenizer under a pressure of 2000 to 3200 kgf/cm$^2$ with a pass number through the homogenizer of 5 to 20 to obtain a fat emulsion consisting essentially of fat particles having a mean particle size of 0.003 to 0.100 μm.

DESCRIPTION OF PREFERRED EMBODIMENTS

Figure 1:
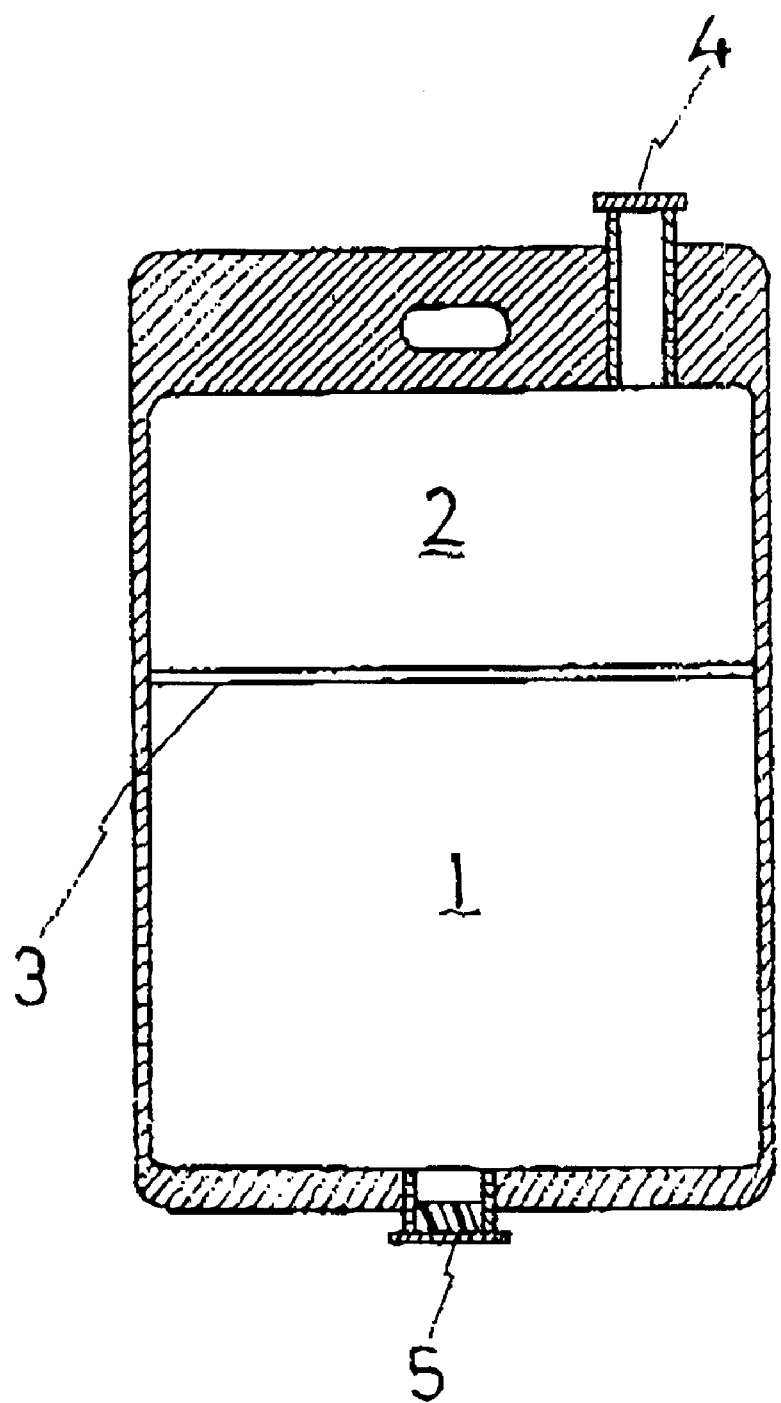
FIG. 1 is a planar view of an infusion container consisting of two chambers containing an inventive infusion preparation.

A fat emulsion (A) used in the present invention consists essentially of particles having a mean particle size of 0.003 to 0.100 μm. Such fat emulsion is a fat emulsion for a nutrition supplement obtained by emulsifying fat and, if necessary, saccharides and/or polyhydric alcohols using an emulsifier.

Fat includes vegetable oils, fish oils, and triglycerides of middle-chain fatty acids or chemically synthesized triglycerides. Those exemplified typically comprise vegetable oils such as soybean oil, safflower oil, olive oil, cottonseed oil, corn oil, palm oil, beefsteak plant oil and sesame oil, as well as fish oils, and synthesized triglycerides of middle- or long-chain fatty acids. Two or more of these materials can also be used in combination. The concentration of the fat in solution (A) is 0.3 to 15.0 g/dL, preferably 0.5 to 2.0 g/dL.

An emulsifier used in the present invention is egg yolk phospholipid, hydrogenated egg yolk phospholipid, soybean phospholipid, hydrogenated soybean phospholipid or a nonionic surfactant. Those exemplified typically comprise a purified egg yolk lecithin, a purified soybean lecithin and hydrogenated derivatives thereof, nonionic surfactants such as Polysorbate 80 and HCO-60 (trade names) and the like. Two or more of these emulsifiers can also be used in combination. The amount of the emulsifier in the present invention is 0.1 to 0.5 part by weight, preferably 0.3 to 0.5 part by weight, per 1 part by weight of fat.

A saccharide used in the present invention can be any of those used customarily in various infusion preparations such as monosaccharides such as glucose and fructose, and disaccharides such as maltose. Among these, a reducing sugar such as glucose, fructose and maltose is particularly preferred.

A polyhydric alcohol used in the present invention can be, for example, glycerol and a polyhydric sugar alcohol. A polyhydric sugar alcohol can be, for example, xylitol, sorbitol, mannitol and the like. Two or more of these saccharides and polyhydric alcohols can also be used in combination. The concentration of the saccharides or the polyhydric alcohols in solution (A) is 0 to 60 g/dL, preferably 10 to 40 g/dL.

Fat emulsion (A) can be, for example, prepared by emulsifying fat in the presence of saccharides and/or polyhydric alcohols to obtain a fat emulsion consisting essentially of fat particles having a mean particle size of 0.003 to 0.100 μm. A typical procedure involves coarse emulsification of a fat using a high speed agitating homogenizer "POLYTRON" (KINEMATICA), followed by addition of water for injection, further followed by fine emulsification using a high pressure spray homogenizer "DeBEE" (BEE International) under a pressure of 2000 to 3200 kgf/cm$^2$, for example, 2800 kgf/cm$^2$, with a pass number through the homogenizer of 5 to 30. Subsequently, a resultant fat emulsion is sterilized by an autoclave, hot water immersion or filtration sterilization.

The coarse emulsified fat particles have a mean particle size of preferably at least 1 μm, more preferably at least 3 μm.

In the present invention, a fat concentration of 0.3 to 15.0 g/dL is sufficient for preventing an essential fatty acid deficiency. At such concentration, by adjusting the amount of an emulsifier to be added, the amounts of saccharides and polyhydric alcohols to be added, the emulsifying pressure and the number of emulsifying cycles so that a mean particle size of the fat particles of 0.003 to 0.100 μm can be obtained, a fat-containing TPN solution exhibiting a satisfactory transparency can be obtained when using either fat emulsion (A) alone or after mixing with solution (B), (B-1) or (B-2). In addition, a fat-containing TPN solution of the present invention can advantageously be filtered through a sterilization filter having a pore size of 0.2 μm before administering to a patient.

Solution (B), (B-1) or (B-2) used in the present invention contains electrolytes and/or amino acids. Such electrolytes can be, for example, a water-soluble salt of inorganic substances such as sodium, potassium, calcium, magnesium, zinc, iron, copper, manganese, iodine, phosphorus and the like; for instance, chloride, sulfate, acetate, gluconate, lactate, or glycerophosphate. Electrolytes such as salts of sodium ion, potassium ion, calcium ion, magnesium ion, chloride ion, phosphate ion and zinc ion are preferred.

An amino acid used in the present invention is an essential amino acid, a non-essential amino acid and/or salts, esters and N-acyl derivatives thereof. Typically, L-isoleucine, L-leucine, L-lysine, L-methionine, L-phenylalanine, L-threonine, L-tryptophan, L-valine, L-alanine, L-arginine, L-aspartic acid, L-cysteine, L-glutamic acid, L-histidine, L-proline, L-serine, L-tyrosine, L-glycine and the like are exemplified. These amino acids can be in the form of inorganic acid salts such as L-arginine hydrochloride, L-cysteine hydrochloride, L-glutamine hydrochloride, L-histidine hydrochloride and L-lysine hydrochloride, organic acid salts such as L-lysine acetate and L-lysine malate, esters such as L-tyrosine methylester, L-methionine methylester and L-methionine ethylester, N-substituted derivatives such as N-acetyl-L-cysteine, N-acetyl-L-tryptophan and N-acetyl-L-proline, and dipeptides such as L-tyrosyl-L-tyrosine, L-alanyl-L-tyrosine, L-arginyl-L-tyrosine and L-tyrosyl-L-arginine.

In the present invention, the nutrient infusion has the constituents listed in the following Table 1. The solution of the present invention is prepared in a standard manner.

TABLE 1

| Component | Concentration | |
|---|---|---|
| Fat | 1.5 to 100.0 | g/L |
| Emulsifier | 0.15 to 50.0 | g/L |
| Saccharide or polyhydric alcohol | 25.0 to 350.0 | g/L |
| L-Isoleucine | 0.5 to 5.5 | g/L |
| L-Leucine | 0.5 to 7.0 | g/L |
| L-Lysine | 0.5 to 7.0 | g/L |
| L-Methionine | 0.1 to 5.0 | g/L |
| L-Phenylalanine | 0.1 to 6.0 | g/L |
| L-Threonine | 0.2 to 3.0 | g/L |
| L-Tryptophan | 0.1 to 2.0 | g/L |
| L-Valine | 0.5 to 6.0 | g/L |
| L-Alanine | 0 to 5.0 | g/L |
| L-Arginine | 0 to 9.0 | g/L |
| L-Aspartic acid | 0 to 2.5 | g/L |
| L-Cysteine | 0 to 0.5 | g/L |
| L-Glutamic acid | 0 to 3.0 | g/L |
| L-Histidine | 0 to 3.5 | g/L |
| L-Proline | 0 to 4.5 | g/L |
| L-Serine | 0 to 3.0 | g/L |
| L-Tyrosine | 0 to 0.4 | g/L |
| Glycine | 0 to 7.0 | g/L |
| Sodium | 20 to 150 | mEq/L |
| Potassium | 10 to 50 | mEq/L |
| Calcium | 0 to 15 | mEq/L |
| Magnesium | 0 to 15 | mEq/L |
| Chloride | 20 to 150 | mEq/L |
| Phosphate | 0 to 15 | mEq/L |
| Zinc | 0 to 100 | μmol/L |

In the present invention, the fat emulsion consisting essentially of fat particles having a mean particle size of 0.003 to 0.100 μm and a dispersion medium, or the solutions containing electrolytes and/or amino acids may also contain saccharides or polyhydric alcohols. When a solution containing amino acids contains saccharides, the pH is preferably acidic. The fat emulsion consisting essentially of fat particles having a mean particle size of 0.003 to 0.100 μm and a dispersion medium, may further contain electrolytes and/or amino acids. The amino acid is preferably a neutral amino acid or an acidic amino acid.

In the present invention, a saccharide component in the fat emulsion rarely undergoes an interaction with oil. In addition, an incorporation of saccharide into a fat emulsion allows the refractive index of an oil phase of the fat emulsion to be close to that of a water phase, resulting in a transparent appearance of the fat emulsion. An additional incorporation of glycerin, which is a polyhydric alcohol; serves to ensure further transparency. Storage of saccharides in a chamber different from that for amino acids serves to avoid a Maillard reaction between the two.

It has been known that the presence of saccharides and polyhydric alcohols during an emulsifying process of an oil can allow the fat particles to be micronized (U.S. Pat. Nos. 5,626,880 and 5,674,527). Smaller fat particles in a fat emulsion cause lower scattering of transmitted light, resulting in higher transparency. Nevertheless, a lower limit of a particle size of a conventional fat emulsion was as large as 0.14 μm. On the contrary, the present invention employs a fat emulsion consisting essentially of particles whose mean particle size is as small as 0.003 to 0.100 μm, preferably 0.010 to 0.100μm, and a dispersion medium. It is difficult to prepare a fat emulsion consisting essentially of particles whose mean particle size is less than 0.003 μm and a dispersion medium, and use of a fat emulsion whose mean particle size is greater than 0.100 μm results in turbidity of 150 degrees or higher even if a large amount of a saccharide and/or a polyhydric alcohol is added.

In the present invention, a fat emulsion-containing TPN solution is transparent even after mixing the above mentioned fat emulsion (A) and solution (B) containing electrolytes and amino acids or solution (B-1) containing electrolytes optionally with solution (B-2) containing amino acids, and can be filtered through a filter having a pore size of 0.2 μm.

A fat emulsion according to the present invention can be obtained by a coarse emulsification of fat followed by fine emulsification using a high pressure spray homogenizer under a pressure of 2000 to 3200 kgf/cm$^2$ with a pass number through the homogenizer of 5 to 30 further followed by sterilization by an autoclave, a hot water immersion or a filtration sterilization. The fat emulsion is stored in a chamber of an infusion container in which a solution containing electrolytes and/or amino acids is also stored.

An infusion container according to the present invention has a plurality of chambers, which are isolated from each other with partitions that are designed to be capable of being easily opened. For example, such an infusion container is a flexible plastic container having a plurality of chambers, wherein all or a part of partitions which isolate the chambers from each other can be opened externally to allow the chambers to communicate with each other. One typically exemplified is an infusion bag which is partitioned into 2 or 3 chambers with sealed barriers, which can be opened immediately before use by pushing the outside of the bag by hand (FIGS. 1 and 2 and as disclosed in Japanese Laid-Open Patent Publication Nos. 8-191873 and 8-182739).

Figure 2:
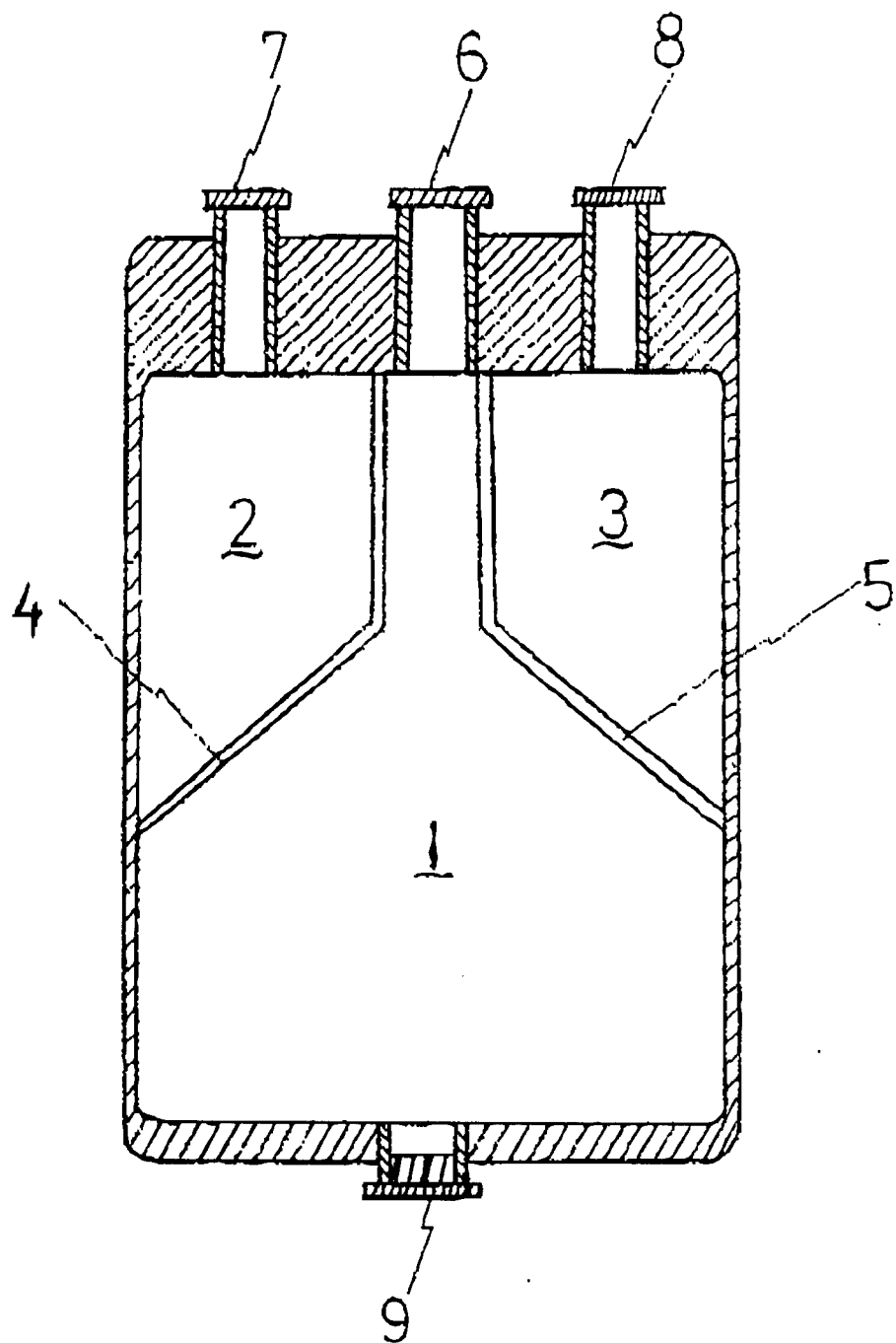
FIG. 2 is a planar view of an infusion container consisting of three chambers containing an inventive infusion preparation.

In FIG. 1, chambers 1 and 2 for storing an infusion preparation are provided together with barrier 3, preparation inlet 4 and outlet 5. In FIG. 2, chambers 1, 2 and 3 each for storing an infusion preparation are provided together with barriers 4 and 5, inlets 6, 7 and 8 and outlet 9. In such infusion container, one chamber can contain a fat emulsion (A) consisting essentially of fat particles having a mean particle size of 0.003 to 0.100 μm and a dispersion medium, and the other chamber can contain solution (B) containing electrolytes and amino acids. Alternatively, one chamber can contain a fat. emulsion (A) consisting essentially of fat particles having a mean particle size of 0.003 to 0.100 μm and the other chambers can contain solution (B-1) containing electrolytes and solution (B-2) containing amino acids, respectively.

An infusion container according to the present invention is not limited to one having 2 or 3 chambers and can have 4 or more chambers for further containing a solution (C) containing saccharides, if necessary.

In the present invention, turbidity of a solution after mixing emulsion (A), solution (B), (B-1) or (B-2) and, if necessary, solution (C) prepared as described above is usually 20 to 150 degrees, preferably 20 to 130 degrees, which allows the mixed solution to be passed through a sterilization filter whose pore size is 0.2 μm. Accordingly, insoluble foreign bodies in the TPN solution, if any, can readily be identified. In addition, it is possible not only to remove aggregated fat particles and insoluble foreign bodies but also to prevent infections with microorganisms.

The present invention is further detailed in the following examples.

Mean particle size and turbidity as shown in Table 4 were determined as follows.

(1) Mean Fat Particle Size

A device for determining particle size and a particle size distribution, NICOMP model 380ZLS (Particle Sizing System) was used to determine the mean particle size of a fat particle in a fat emulsion by a dynamic laser light scattering method.

(2) Transparency of Fat Emulsion

Using a light absorption photometer U-3000 (HITACHI), turbidity of a fat emulsion was determined using the absorbance of 1 mg/L of kaolin at 660 nm as 1.

The compositions of the infusion preparations, fat emulsion (A), and solutions (B) and (C) used in Examples 1 to 7 and Comparative Examples 1 to 3 are shown in Table 2. The numeric data are concentrations of respective solutions.

TABLE 2

|  |  | Unit | Ex. 1 | Ex. 2 | Ex. 3 | Ex. 4 | Ex. 5 | Ex. 6 | Ex. 7 | Comp. Ex. 1 | Comp. Ex. 2 | Comp. Ex. 3 |
|---|---|---|---|---|---|---|---|---|---|---|---|---|
| Volume | Emulsion (A) | mL | 1200 | 1200 | 500 | 500 | 500 | 40 | 900 | 500 | 40 | 500 |
|  | Solution (B) | mL | 300 | 300 | 300 | 300 | 300 | 300 | 100 | 300 | 300 | 300 |
|  | Solution (C) | mL | — | 360 | — | — | — | 600 | — | 600 | 600 | — |
| Emulsion A | Soybean oil | g/dL | 0.3 | 0.3 | 1 | 1 | 1 | 15 | 0.5 | 1 | 20 | 1 |
|  | Egg yolk lecithin | g/dL | 0.03 | 0.15 | 0.25 | 0.5 | 0.5 | 7.5 | 0.25 | 0.5 | 10 | 0.5 |
|  | Glucose | g/dL | 20 | — | 30 | 30 | 30 | 60 | 10 | — | 50 | 30 |
|  | Glycerol | g/dL | — | — | — | — | 5 | — | — | — | — | 5 |
| Solution B | Amino acid | g/dL |  |  | 30 |  |  |  | 20 |  | 30 |  |
|  | Sodium | mEq |  |  |  |  |  | 35 |  |  |  |  |
|  | Potassium | mEq |  |  |  |  |  | 27 |  |  |  |  |
|  | Calcium | mEq |  |  |  |  |  | 6 |  |  |  |  |
|  | Magnesium | mEq |  |  |  |  |  | 4.8 |  |  |  |  |
|  | Chloride | mEq |  |  |  |  |  | 40.5 |  |  |  |  |
|  | Phosphate | mmol |  |  |  |  |  | 12 |  |  |  |  |
|  | Zinc | μmol |  |  |  |  |  | 10 |  |  |  |  |
| Solution C | Glucose | g/dL | — | 50 | — | — | — | 30 | — | 30 | 30 | — |

EXAMPLE 1

Fat emulsion (A): 3.6 g of a purified soybean oil and 0.36 g of a purified egg yolk lecithin were mixed uniformly and dissolved together with 240 g of glucose in an appropriate amount of water for injection. The mixture was subjected to a high speed agitating homogenizer "POLYTRON" (KINEMATICA) to obtain a coarse emulsion. The coarse emulsion thus obtained was combined with water for injection to make 1200 mL in total, which was subjected to a high pressure spray homogenizer "DeBEE" (BEE International) under a pressure of 2800 kgf/cm$^2$ with a pass number through the homogenizer of 25, thereby effecting a fine emulsification. The fat emulsion thus obtained was sterilized by an autoclave. The mean particle size obtained was 0.0978 μm.

Solution (B): Using a composition shown in Table 4, a solution containing amino acids and electrolytes was prepared, and sterilized by an autoclave.

The mean particle size and the turbidity of fat emulsion (A) thus obtained are shown in Table 4. Fat emulsion (A) and solution (B) were combined in a ratio shown in Table 2 to obtain a mixture whose turbidity and filtration characteristics through a sterilization filter having a pore size of 0.2 μm (NIPRO, Filter set FG-20BY, pore size: 0.2 μm) are also shown in Table 4.

The compositions of solutions (B) in the Examples and Comparative Examples are identical to each other. The composition is shown in Table 3.

TABLE 3

| Component | Unit |  |
|---|---|---|
| L-Isoleucine | g/L | 1.0 |
| L-Leucine | g/L | 1.0 |
| L-Lysine acetate | g/L | 1.05 |
| L-Methionine | g/L | 0.5 |
| L-Phenylalanine | g/L | 0.75 |
| L-Threonine | g/L | 0.75 |
| L-Tryptophan | g/L | 0.25 |
| L-Valine | g/L | 1.0 |
| L-Alanine | g/L | 0.75 |
| L-Arginine | g/L | 1.0 |
| L-Aspartic acid | g/L | 0.1 |
| L-Cysteine | g/L | 0.1 |
| L-Glutamic acid | g/L | 0.1 |
| L-Histidine | g/L | 0.5 |
| L-Proline | g/L | 0.5 |
| L-Serine | g/L | 0.15 |
| L-Tyrosine | g/L | 0.05 |
| Glycine | g/L | 0.75 |
| Sodium chloride | g/L | 1.71 |
| Potassium chloride | g/L | 1.31 |
| Potassium | g/L | 7.89 |

TABLE 3-continued

| Component | Unit | |
|---|---|---|
| glycerophosphate | | |
| Magnesium sulfate | g/L | 2.18 |
| Calcium gluconate | g/L | 3.16 |
| Sodium acetate anhydride | g/L | 6.03 |
| Zinc sulfate | g/L | 0.0084 |

EXAMPLE 2

Fat emulsion (A): 3.6 g of a purified soybean oil and 1.8 g of a purified egg yolk lecithin were mixed uniformly and combined with an appropriate amount of water for injection, and then subjected to a high speed agitating homogenizer to obtain a coarse emulsion. The coarse emulsion thus obtained was combined with water for injection to make 1200 mL in total, which was subjected to a high pressure spray homogenizer "DeBEE" under a pressure of 2800 $kgf/cm^2$ with a pass number through the homogenizer of 25, thereby effecting a fine emulsification. The fat emulsion thus obtained was sterilized by an autoclave. The mean particle size obtained was 0.0519 $\mu$m.

Solution (B): solution (B) prepared by the same method as that of Example 1.

Solution (C): 180 g of glucose was dissolved in an appropriate volume of water for injection to make 360 mL in total. The glucose solution thus obtained was sterilized by an autoclave.

The mean particle size and the turbidity of fat emulsion (A) determined in the same manner as in Example 1 are shown in Table 4. The turbidity and the filtration characteristics through a sterilization filter having a pore size of 0.2 $\mu$m of fat emulsion (A), and solutions (B) and (C), which were combined in a ratio as shown in Table 2 are also shown in Table 4.

EXAMPLE 3

Fat emulsion (A): 5 g of a purified soybean oil and 1.25 g of a purified egg yolk lecithin were mixed uniformly and dissolved together with 150 g of glucose in an appropriate amount of water for injection. The mixture was subjected to a high speed agitating homogenizer to obtain a coarse emulsion.

The coarse emulsion thus obtained was combined with water for injection to make 500 mL in total, which was subjected to a high pressure spray homogenizer DeBEE under a pressure of 2800 $kgf/cm^2$ with a pass number through the homogenizer of 25, thereby effecting a fine emulsification. The fat emulsion thus obtained was sterilized by an autoclave. The mean particle size obtained was 0.0585 $\mu$m.

Solution (B): solution (B) prepared by the same method as that of Example 1.

The mean particle size and the turbidity of fat emulsion (A) determined in the same manner as in Example 1 are shown in Table 4. The turbidity and the filtration characteristics through a sterilization filter having a pore size of 0. 2 $\mu$m of fat emulsion (A) and solution (B) which were combined in a ratio as shown in Table 2 are also shown in Table 4.

EXAMPLE 4

Fat emulsion (A): 5 g of a purified soybean oil and 2.5 g of a purified egg yolk lecithin were mixed uniformly and dissolved together with 150 g of glucose in an appropriate amount of water for injection. The mixture was subjected to a high speed agitating homogenizer to obtain a coarse emulsion. The coarse emulsion thus obtained was combined with water for injection to make 500 mL in total, which was subjected to a high pressure spray homogenizer DeBEE under a pressure of 2800 $kgf/cm^2$ with a pass number through the homogenizer of 25, thereby effecting a fine emulsification. The fat emulsion thus obtained was sterilized by an autoclave. The mean particle size obtained was 0.0386 $\mu$m.

Solution (B): solution (B) prepared by the same method as that of Example 1.

The mean particle size and the turbidity of fat emulsion (A) determined in the same manner as in Example 1 are shown in Table 4. The turbidity and the filtration characteristics through a sterilization filter having a pore size of 0.2 $\mu$m of fat emulsion (A) and solution (B) which were combined in a ratio as shown in Table 2 are also shown in Table 4.

EXAMPLE 5

Fat emulsion (A): 5.0 g of a purified soybean oil and 2.5 g of a purified egg yolk lecithin were mixed uniformly and dissolved together with 25 g of concentrated glycerin and 150 g of glucose in an appropriate amount of a water for injection. The mixture was subjected to a high speed agitating homogenizer to obtain a coarse emulsion. The coarse emulsion thus obtained was combined with water for injection to make 500 mL in total, which was subjected to a high pressure spray homogenizer DeBEE under a pressure of 2800 $kgf/cm^2$ with a pass number through the homogenizer of 25, thereby effecting a fine emulsification. The fat emulsion thus obtained was sterilized by an autoclave. The mean particle size obtained was 0.0265 $\mu$m.

Solution (B): solution (B) prepared by the same method as that of Example 1.

The mean particle size and the turbidity of fat emulsion (A) determined in a manner similar to that in Example 1 are shown in Table 4. The turbidity and the filtration characteristics through a sterilization filter having a pore size of 0. 2 $\mu$m of fat emulsion (A) and solution (B) which were combined in a ratio as shown in Table 2 are also shown in Table 4.

EXAMPLE 6

Fat emulsion (A): 75 g of a purified soybean oil and 37.5 g of a purified egg yolk lecithin were mixed uniformly and dissolved together with 300 g of glucose in an appropriate amount of water for injection, and the mixture was subjected to a high speed agitating homogenizer to obtain a coarse emulsion. The coarse emulsion thus obtained was combined with water for injection to make 500 mL in total, which was subjected to a high pressure spray homogenizer DeBEE under a pressure of 2800 $kgf/cm^2$ with a pass number through the homogenizer of 25, thereby effecting a fine emulsification. The fat emulsion thus obtained was sterilized by an autoclave. The mean particle size obtained was 0.0505 $\mu$m.

Solution (B): solution (B) prepared by the same method as that of Example 1.

Solution (C): 180 g of glucose was dissolved in an appropriate volume of water for injection to make 600 mL in total. The glucose solution thus obtained was sterilized by an autoclave.

The mean particle size and the turbidity of fat emulsion (A) determined in the same manner as in Example 1 are shown in Table 4. The turbidity and the filtration characteristics through a sterilization filter having a pore size of 0.2 μm of fat emulsion (A), and solutions (B) and (C), which were combined in a ratio as shown in Table 2 are also shown in Table 4.

EXAMPLE 7

Fat emulsion (A): 4.5 g of a purified soybean oil and 2.25 g of a purified egg yolk lecithin were dissolved together with 90 g of glucose in an appropriate amount of water for injection, and the mixture was subjected to a high speed agitating homogenizer to obtain a coarse emulsion. The coarse emulsion thus obtained was combined with water for injection to make 900 mL in total, which was subjected to a high pressure spray homogenizer DeBEE (BEE International) under a pressure of 2800 kgf/cm² with a pass number through the homogenizer of 25, thereby a fine emulsification was effected. The fat emulsion thus obtained was sterilized by an autoclave. The mean particle size obtained was 0.0502 μm.

Solution (B): Using a composition as shown in Table 3, a solution containing amino acids and electrolytes was prepared, and sterilized by an autoclave.

The mean particle size and the turbidity of solution (A) determined in the same manner as in Example 1 are shown in Table 4. The turbidity and the filtration characteristics through a sterilization filter having a pore size of 0.2 μm of fat emulsion (A) and solution (B) which were combined in a ratio as shown in Table 2 are also shown in Table 4.

Comparative Example 1

Fat emulsion (A): 5 g of a purified soybean oil and 2.5 g of a purified egg yolk lecithin were mixed uniformly and combined with an appropriate amount of water for injection, and the mixture was subjected to a high speed agitating homogenizer to obtain a coarse emulsion. The coarse emulsion thus obtained was combined with water for injection to make 500 mL in total, which was subjected to a high pressure spray homogenizer DeBEE under a pressure of 2800 kgf/cm² with a pass number through the homogenizer of 25, thereby a fine emulsification was effected. The fat emulsion thus obtained was sterilized by an autoclave. The mean particle size obtained was 0.0520 μm.

Solution (B): solution (B) prepared by the same method as that of Example 1.

Solution (C): 180 g of glucose was dissolved in an appropriate volume of water for injection to make 600 mL in total. The glucose solution thus obtained was sterilized by an autoclave.

The mean particle size and the turbidity of fat emulsion (A) determined in the same manner as in Example 1 are shown in Table 4. The turbidity and the filtration characteristics through a sterilization filter having a pore size of 0.2 μm of fat emulsion (A), and solutions (B) and (C), which were combined in a ratio as shown in Table 2 are also shown in Table 4. The turbidity of fat emulsion (A) was 150 or higher, and the turbidity after mixing was also 150 or higher.

Comparative Example 2

Fat emulsion (A): 100 g of a purified soybean oil and 50 g of a purified egg yolk lecithin were mixed uniformly and dissolved together with 250 g of glucose in an appropriate amount of a water for injection, and the mixture was subjected to a high speed agitating homogenizer to obtain a coarse emulsion. The coarse emulsion thus obtained was combined with water for injection to make 500 mL in total, which was subjected to a high pressure spray homogenizer DeBEE under a pressure of 2800 kgf/cm² with a pass number through the homogenizer of 25, thereby effecting a fine emulsification. The fat emulsion thus obtained was sterilized by an autoclave. The mean particlegeize obtained was 0.0777 μm.

Solution (B): solution (B) prepared by the same method as that of Example 1.

Solution (C): 180 g of glucose was dissolved in an appropriate volume of water for injection to make 600 mL in total. The glucose solution thus obtained was sterilized by an autoclave.

The mean particle size and the turbidity of fat emulsion (A) determined in the same manner as in Example 1 are shown in Table 4. The turbidity and the filtration characteristics through a sterilization filter having a pore size of 0.2 μm of fat emulsion (A), and solutions (B) and (C), which were combined in a ratio as shown in Table 2 are also shown. The turbidity of fat emulsion (A) could not be determined, and the turbidity after mixing also could not be determined.

Comparative Example 3

Fat emulsion (A): 5.0 g of a purified soybean oil and 2.5 g of a purified egg yolk lecithin were mixed uniformly and combined with 25 g of concentrated glycerin and 150 g of glucose dissolved in an appropriate amount of water for injection, and the mixture was subjected to a high speed agitating homogenizer to obtain a coarse emulsion.

The coarse emulsion thus obtained was combined with water for injection to make 500 mL in total, which was subjected to a high pressure spray homogenizer DeBEE under a pressure of 750 kgf/cm² with a pass number through the homogenizer of 25, thereby effecting a fine emulsification. The fat emulsion thus obtained was sterilized by an autoclave. The mean particle size obtained was 0.1731 μm.

Solution (B): solution (B) prepared by the same method as that of Example 1.

The mean particle and the turbidity of fat emulsion (A) determined in the same manner as in Example 1 are shown in Table 4. The turbidity and the filtration characteristics through a sterilization filter having a pore size of 0.2 μm of fat emulsion (A) and solution (B) which were combined in a ratio as shown in Table 2 are also shown in Table 4. The turbidity of fat emulsion (A) could not be determined, and the turbidity after mixing could also not be determined.

TABLE 4

| Determination item Unit | Mean particle size of Emulsion (A) μm | Turbidity of Emulsion (A) Degree | Turbidity after mixing Degree | Filtration characteristics through 0.20 μm filter |
|---|---|---|---|---|
| Example 1 | 0.0978 | 121.3 | 100.5 | passed |
| Example 2 | 0.0519 | 60.08 | 51.58 | passed |
| Example 3 | 0.0585 | 88.47 | 75.20 | passed |
| Example 4 | 0.0386 | 68.64 | 55.03 | passed |
| Example 5 | 0.0265 | 32.36 | 26.41 | passed |
| Example 6 | 0.0505 | 107.95 | 122.77 | passed |
| Example 7 | 0.0502 | 135.03 | 126.49 | passed |
| Comparative Example 1 | 0.052 | 150 degree or higher | 150 degree or | — |

TABLE 4-continued

| Determination item Unit | Mean particle size of Emulsion (A) μm | Turbidity of Emulsion (A) Degree | Turbidity after mixing Degree | Filtration characteristics through 0.20 μm filter |
|---|---|---|---|---|
| Comparative Example 2 | 0.0777 | Could not detected | higher Could not detected | — |
| Comparative Example 3 | 0.1731 | Could not detected | Could not detected | — |

As evident from Table 4, the turbidity was 150 degrees or higher when no saccharide or no polyhydric alcohol was contained even if the concentration of the fat in fat emulsion (A) was 1.0 g/dL (Comparative Example 1). The emulsion became turbid when the concentration of fat was high even if a large amount of a saccharide and polyhydric alcohol (Comparative Example 2) were contained. The emulsion became turbid also when the mean particle size became far larger than 0.100 μm even if the composition was quite the same as that of Example 5 (Comparative Example 3). An inventive nutrient infusion preparation gave a turbidity of fat emulsion (A) of 30 to 150 and a turbidity of solution (B) optionally mixed with solution (C) of 20 to 150, exhibiting an excellent transparency, which was due to a mean particle size of 0.003 to 0.100 μm.

EXAMPLE 8

Fat emulsion (A) and solution (B) prepared in Example 1 were contained individually in the two chambers in an infusion container as shown in FIG. 1. Just before use, the barriers were opened by an external force to mix the contents with each other, and the mixed solution was allowed to pass through a sterilization filter having a pore size of 0.20 μm.

An infusion preparation according to the present invention contains the essential components in a conventional TPN solution such as saccharides, electrolytes and amino acids together with fats, thereby providing a remedy and prevention of an essential fatty acid deficiency, which is a side effect during TPN therapy. It also enables administration to a patient after filtration through a sterilization filter having a pore size of 0.20 μm or less, because of which it is possible not only to remove aggregated fat particles and insoluble foreign bodies but also to prevent infections with microorganisms. In addition, an appreciable transparency of fat emulsion (A) enables a visual identification of insoluble foreign bodies present in an infusion container. A high transparency of fat emulsion (A) and solution (B), (B-1) or (B-2) optionally mixed with solution (C) makes the preparation familiar and tolerable to a patient. Such advantage is not limited to TPN therapy, and can also be achieved even if the nutrition is supplied via a peripheral vein provided that an appropriate composition of the preparation is selected.

What is claimed is:

1. A nutrient infusion preparation comprising a fat emulsion consisting essentially of fat particles having a mean particle size of 0.003 to 0.0978 μm and a dispersion medium, wherein the fat emulsion contains 0.3 to 15.0 g/dL of fat, 10 to 60 g/dL of a saccharide and/or a polyhydric alcohol, and an emulsifier selected from the group consisting of egg yolk phospholipid, hydrogenated egg yolk phospholipid, soybean phospholipid and hydrogenated soybean phospholipid, and the turbidity of said nutrient infusion preparation expressed as absorbance at 660 nm is 20 to 150 degrees; and a solution containing electrolytes and/or amino acids.

2. A nutrient infusion preparation comprising a fat emulsion consisting essentially of fat particles having a mean particle size of 0.003 to 0.0978 μm, a saccharide and/or a polyhydric alcohol, and a dispersion medium, wherein the fat concentration of the emulsion is 0.3 to 15.0 g/dL; and a solution containing electrolytes and amino acids.

3. A nutrient infusion preparation comprising a fat emulsion consisting essentially of fat particles having a mean particle size of 0.003 to 0.0978 μm, a saccharide and/or a polyhydric alcohol, and a dispersion medium, wherein the fat concentration of the emulsion is 0.3 to 15.0 g/dL; a solution containing electrolytes and a solution containing amino acids.

4. A nutrient infusion preparation according to claim 1, 2 or 3 wherein at least one of said solutions contains a saccharide and/or a polyhydric alcohol.

5. A nutrient infusion preparation according to claim 1, 2 or 3 wherein said fat emulsion further contains electrolytes and/or amino acids.

6. A nutrient infusion preparation according to claim 1, 2 or 3 wherein said fat emulsion is a fat emulsion for supplementing nutrition which is obtained by emulsifying a fat in water using an emulsifier in the presence of a saccharide and/or a polyhydric alcohol.

7. A nutrient infusion preparation according to claim 1, 2 or 3 wherein said fat emulsion is a fat emulsion for supplementing nutrition which is obtained by emulsifying a fat in water using an emulsifier, and wherein 0.1 to 0.5 part by weight of said emulsifier is incorporated per 1 part by weight of fat.

8. A nutrient infusion preparation according to claim 1, 2 or 3 having the constituents listed in the following table:

| Component | Concentration | |
|---|---|---|
| Fat | 1.5 to 100.0 | g/L |
| Emulsifier | 0.15 to 50.0 | g/L |
| Saccharide or polyhydric alcohol | 25.0 to 350.0 | g/L |
| L-Isoleucine | 0.5 to 5.5 | g/L |
| L-Leucine | 0.5 to 7.0 | |
| L-Lysine | 0.5 to 7.0 | g/L |
| L-Methionine | 0.1 to 5.0 | g/L |
| L-Phenylalanine | 0.1 to 6.0 | g/L |
| L-Threonine | 0.2 to 3.0 | g/L |
| L-Tryptophan | 0.1 to 2.0 | g/L |
| L-Valine | 0.5 to 6.0 | g/L |
| L-Alanine | 0 to 5.0 | g/L |
| L-Arginine | 0 to 9.0 | g/L |
| L-Aspartic acid | 0 to 2.5 | g/L |
| L-Cysteine | 0 to 0.5 | g/L |
| L-Glutamic acid | 0 to 3.0 | g/L |
| L-Histidine | 0 to 3.5 | g/L |
| L-Proline | 0 to 4.5 | g/L |
| L-Serine | 0 to 3.0 | g/L |
| L-Tyrosine | 0 to 0.4 | g/L |
| Glycine | 0 to 7.0 | g/L |
| Sodium | 20 to 150 | mEq/L |
| Potassium | 10 to 50 | mEq/L |
| Calcium | 0 to 15 | mEq/L |
| Magnesium | 0 to 15 | mEq/L |
| Chloride | 20 to 150 | mEq/L |
| Phosphate | 0 to 15 | mEq/L |
| Zinc | 0 to 100 | μmol/L |

9. A container for a nutrient infusion preparation comprising a container having a plurality of chambers isolated from each other by partitions capable of being easily opened, wherein one chamber contains a fat emulsion consisting essentially of fat particles having a mean particle size of 0.003 to 0.0978 μm and a dispersion medium, and the other chamber contains a solution containing electrolytes and/or amino acids.

10. A container for a nutrient infusion preparation comprising a container having a plurality of chambers isolated from each other by partitions capable of being easily opened, wherein one chamber contains a fat emulsion consisting essentially of fat particles having a mean particle size of 0.003 to 0.0978 µm and a dispersion medium, and the other chamber contains a solution containing electrolytes and amino acids.

11. A container for a nutrient infusion preparation comprising a container having a plurality of chambers isolated from each other by partitions capable of being easily opened, wherein one chamber contains a fat emulsion consisting essentially of fat particles having a mean particle size of 0.003 to 0.0978 µm and a dispersion medium and the other chambers respectively contain a solution containing electrolytes and a solution containing amino acids.

12. A method for producing a fat emulsion comprising finely emulsifying a coarse emulsion using a high pressure spray homogenizer under a pressure of 2000 to 3200 kgf/cm$^2$ with a pass number through a homogenizer of 5 to 20, said coarse emulsion containing 0.3 to 15.0 g/dL of fat, 10 to 60 g/dL of a saccharide and/or a polyhydric alcohol, and an emulsifier selected from the group consisting of egg yolk phospholipid, hydrogenated egg yolk phospholipid, soybean phospholipid and hydrogenated soybean phospholipid, to obtain a fat emulsion consisting essentially of fat particles having a mean particle size of 0.003 to 0.0978 µm and a dispersion medium.

* * * * *